(12) United States Patent
Culp

(10) Patent No.: US 7,228,624 B2
(45) Date of Patent: Jun. 12, 2007

(54) METHODS FOR CONNECTING WIRES

(75) Inventor: Gordon W. Culp, Van Nuys, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 139 days.

(21) Appl. No.: 11/097,417

(22) Filed: Apr. 1, 2005

(65) Prior Publication Data

US 2006/0218783 A1   Oct. 5, 2006

(51) Int. Cl.
*H01R 43/04* (2006.01)

(52) U.S. Cl. .......................... 29/861; 29/862; 29/863; 72/402

(58) Field of Classification Search .................. 29/861, 29/862, 863; 72/402
See application file for complete search history.

(56) References Cited

U.S. PATENT DOCUMENTS

| | | | | |
|---|---|---|---|---|
| 2,411,838 A | * | 11/1946 | Swengel | 72/409.14 |
| 2,722,146 A | * | 11/1955 | Byrem | 29/751 |
| 2,765,688 A | * | 10/1956 | Evans | 72/404 |
| 3,523,351 A | * | 8/1970 | Filia | 29/751 |
| 4,534,107 A | * | 8/1985 | Maack | 29/751 |
| 5,692,294 A | * | 12/1997 | Casey | 29/753 |
| 5,934,136 A | * | 8/1999 | Bracher et al. | 72/397 |
| 6,564,610 B2 | * | 5/2003 | Lefavour et al. | 72/453.16 |
| 6,990,843 B2 | * | 1/2006 | Frenken | 72/402 |
| 7,096,573 B2 | * | 8/2006 | Holliday | 29/751 |

* cited by examiner

*Primary Examiner*—Carl J. Arbes
(74) *Attorney, Agent, or Firm*—Gary D. Schnittgrund

(57) ABSTRACT

The invention is a methods of connecting wire that is suitable to connect electrical devices implanted in a living body. The invention enables manipulation of a narrow wire and a crimping component that are on the order of a millimeter in size. The method utilizes a crimper having a slideably attached connector holder that moves relative to the crimper to position an open end of the crimp connector between the crimp die and the crimp anvil, and a slideably attached wire holder that allows the wire holder to be moved relative to the crimper to position a portion of the wire within the open end of the crimp connector. Small components are positioned with precision using a combination of the user's senses, not necessarily including vision. The method does not require stripping electrical insulation from the wires and is also useful for interconnection of miniaturized non-medical electrical devices.

9 Claims, 12 Drawing Sheets

METHODS FOR CONNECTING WIRES

BACKGROUND OF THE INVENTION

The invention relates in general to joining of electrical conductors and more specifically to devices and methods for connecting medical wires.

Medical wires, also sometimes referred to as biomedical wires and leads, provide electrical paths between different locations within a host. Medical wires are typically very thin, insulated wires formed of materials that are compatible with biological substances and which can be implanted into a host to provide electrical connections between medical devices, connectors, electrodes and other wires. Techniques include implanting medical devices such as, for example, sensors and stimulators into living tissue. These medical devices are often connected to an electrode through a medical wire that allows electrical energy to travel between the implanted medical device and the electrode. Such an arrangement is useful in situations where the medical device can not be implanted at the sensing or stimulation target area of the tissue due to size or other limitations. Other medical techniques also require the use of insulated electrical conductors such as medical wires and surgical wires to mechanically and electrically connect devices, connectors and other wires.

Conventional techniques for connecting medical wires are significantly limited. For example, wire connection techniques that include welding are less than optimum due to the limited types of materials that can be welded and convenience issues. All implanted materials must provide long-term compatibility with the host such that tissue inflammation, cellular alteration, and other adverse reactions are avoided or minimized. In addition, the materials should not be susceptible to damage or deterioration due to chemicals, electrolytes and other substances present in the host. Many biologically compatible materials can not be welded to other biologically compatible materials. For example, titanium and titanium alloys can not be welded to platinum, iridium or alloys of platinum and iridium. In addition, the use of welding equipment is often inconvenient and impractical. Welding at a surgery location, for example, can not be easily facilitated.

Other techniques for connecting medical wires include crimping connectors to the medical wire or device. Such connectors may include metal sleeves or tubes that are crimped around the conductor of a medical wire. Many conventional crimping techniques, however, are limited in that the insulation on the medical wire must be stripped before crimping. The insulation is difficult to remove. Further, insulation particles may irritate healing tissue and cause other adverse effects if the wire is stripped at the surgical site. Most methods of removing insulation cause changes in the chemical composition of the insulation resulting in the creation of pyrogens or toxic byproducts. Other crimping techniques are further limited by the awkward crimping tools that are difficult to use with the small and delicate medical wires, connectors and devices that require precision assembly to form a reliable and sturdy connection.

Accordingly, there is need for device and a method for easily, efficiently, and conveniently connecting medical wires that result in reliable electrical connections.

DETAILED DESCRIPTION OF THE INVENTION

In accordance with an exemplary embodiment of the invention, a crimping device facilitates the connection of a crimp connector to a wire by holding the crimp connector and wire in a preferred relative position within a crimping assembly. A connector holder and a wire holder maintain the position of an end of the wire within an open end of the crimp connector while the operator activates the crimping device to squeeze the open end of the crimp connector between a crimp die and crimp anvil of the crimping assembly. A portion of the crimp connector is forced through the insulation of the wire to make an electrical connection. The crimping device can be used at a surgical site by a single operator to easily make reliable connections to wires such as medical wires without the use of awkward welding equipment and while minimizing complications due to insulation debris. In a second exemplary embodiment, a device holder holds a medical device to further facilitate the crimping process when the crimp connector is attached to the medical device. The exemplary crimping device discussed below, therefore, facilitates an efficient and accurate method of crimping small connectors to delicate insulated wires such as medical wires. In some circumstances, the dimensions and arrangements of the crimping device components may be modified to accommodate other types of wires and connectors.

Figure 1:
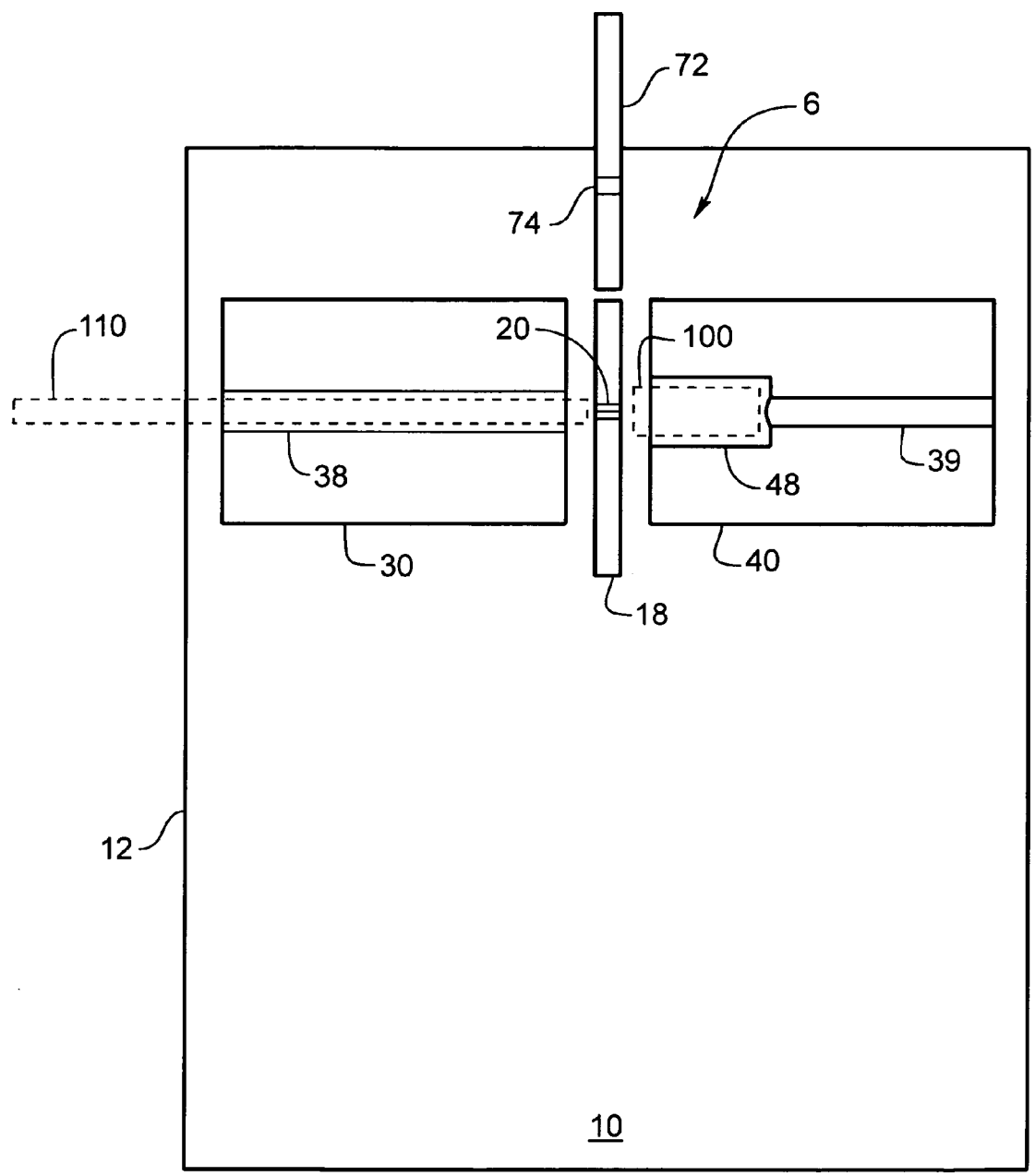
FIG. 1 is a block diagram of a top view of a connector holder and a wire holder connected to a crimping assembly in accordance with an exemplary embodiment of the invention.

FIG. 1 is a block diagram of a top view of a connector holder 40 and a wire holder 30 connected to a crimping assembly 6 in accordance with an exemplary embodiment of the invention. FIG. 1 includes various blocks that represent components, regions, and areas of the crimping device 10 in an illustrated arrangement that indicates some of the relative sizes and positions of the represented components, regions and areas. The blocks and components illustrated in FIG. 1, however, are not necessarily to scale and do not necessarily represent all of the relative sizes, positions and shapes of the components or regions of the crimping device 10.

In the exemplary embodiment of the invention, a crimp connector 100 is connected to a medical wire 110 by crimping the crimp connector 100 such as metal sleeve or tube to the insulated medical wire 110 using a crimper assembly 6 while the crimp connector 100 is held by a connector holder 40 connected to the crimper assembly 6. A wire holder 30 holds the medical wire 110 while the relative positions of the connector holder 40 and the wire holder 30 are changed to position an end of the medical wire 110 within an open end of the crimp connector 100. The crimp connector 100 is positioned between a crimp die 74 and a crimp anvil 20 of the crimper assembly 6. In the exemplary embodiment, the crimp die 74 is formed on a crimp lever 72 and the crimp anvil 20 is formed on an anvil boss 18. The crimp lever 74 rotates about a pivot to align the crimp die 74 with the crimp anvil 20 when the crimp lever 72 and the anvil boss 18 are squeezed together. As the crimp connector 100 is squeezed between the crimp die 74 and the crimp anvil 20, the crimp die 74 forces a portion of the crimp connector 100 through the insulation of the medical wire 110 to form an electrical connection between the crimp connector 100 and the conductor of the medical wire 110.

In the exemplary embodiment, both the connector holder 40 and the wire holder 30 are slideably attached to the crimper assembly 6 allowing both holders 30, 40 to move toward each other. The crimping device 10 includes a base 12 in the exemplary embodiment that facilitates the connection of the crimper assembly 6 to the connector holder 40 and the wire holder 30. Other techniques, however, may be used to attach the connector holder 40 and the wire holder 30 to the crimping assembly 6 in some circumstances. As explained below in further detail, the operator places the medical wire 110 in the wire holder 30 such that an end of the medical wire 110 extends past the edge of wire holder 30. The crimp connector 100 is placed in the connector holder 40 such that the open end of the crimp connector 110 extends past the edge of the connector holder 40. The connector holder 40 and the wire holder 30 are moved toward each other to position the end of the medical wire 110 within the open end of the crimp connector 100. When the holders 30, 40 are in the closed position, the open end of the crimp connector 100 is positioned between the crimp lever 72 and the crimp anvil 20. The crimp connector 100 and the medical wire 110 are shown as dashed-line boxes to illustrate that the crimp connector 100 and the medical wire 110 are inserted and removed during operation and are not part of the crimping device 10. In the exemplary embodiment, the edge of the crimp connector 100 and the end of the medical wire 110 abut the edges of the anvil boss 18 before the holders 30, 40 are moved toward each other to insert the medical wire 110 within the crimp connector 100.

Although the connector holder 40 may include any of several configurations and mechanisms for holding the crimp connector 100, the crimp connector 100 is held within a tube-and-lead groove 48 of the connector holder 40 in the exemplary embodiment. As discussed below, a connector retainer (not shown) further secures the crimp connector 100 within the groove 48. The connector holder 40 includes a lead holder 39 to hold a lead connected to the crimp connector 100 in some circumstances. The lead holder 39 may be useful where a biomedical device is connected to the crimp connector 100 by a section of medical wire (lead). Further, the medical wire (lead) that is connected to the crimp connector 100 may be any type of suitable wire, medical wire or biomedical wire that may be implanted in a host, connected to other devices or connectors or may include only a section of wire. Those skilled in the art will recognize that the lead may be referred to as a lead, wire, medical wire, extension wire, connection wire or by other terms.

The wire holder 30 includes any of several configurations and mechanisms for holding the medical wire 110. In the exemplary embodiment, the wire holder 30 includes a wire groove 38 for holding the medical wire 110. A wire retainer (not shown) further secures the medical wire 110 in the exemplary embodiment.

Figure 2:
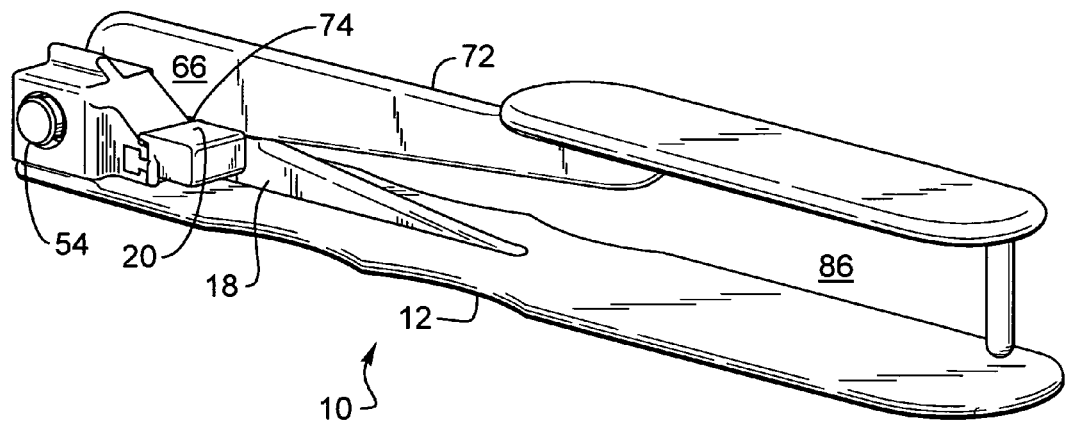
FIG. 2 is an illustration of a perspective view of the crimping device in a closed position in accordance with the exemplary embodiment of the invention.

FIG. 2 is an illustration of a perspective view of the crimping device 10 in a closed position in accordance with the exemplary embodiment of the invention. The exemplary crimping device 10 may be constructed using a variety of techniques, components and arrangements. As described above, the crimping device 10 includes a crimp die 74 on a crimp lever 72 and a crimp anvil 20 on an anvil boss 18 in the exemplary embodiment. The anvil boss 18 is attached to the base 12 that is hingeably attached to the crimp lever 72 by a pin 54 to form a pliers-type assembly facilitating use of the crimping device 10 as a hand tool. The crimper assembly 6 (FIG. 1) is located within a crimping area 66. A protected storage area 86 is formed between the base 12 and the lever 72.

Figure 3:
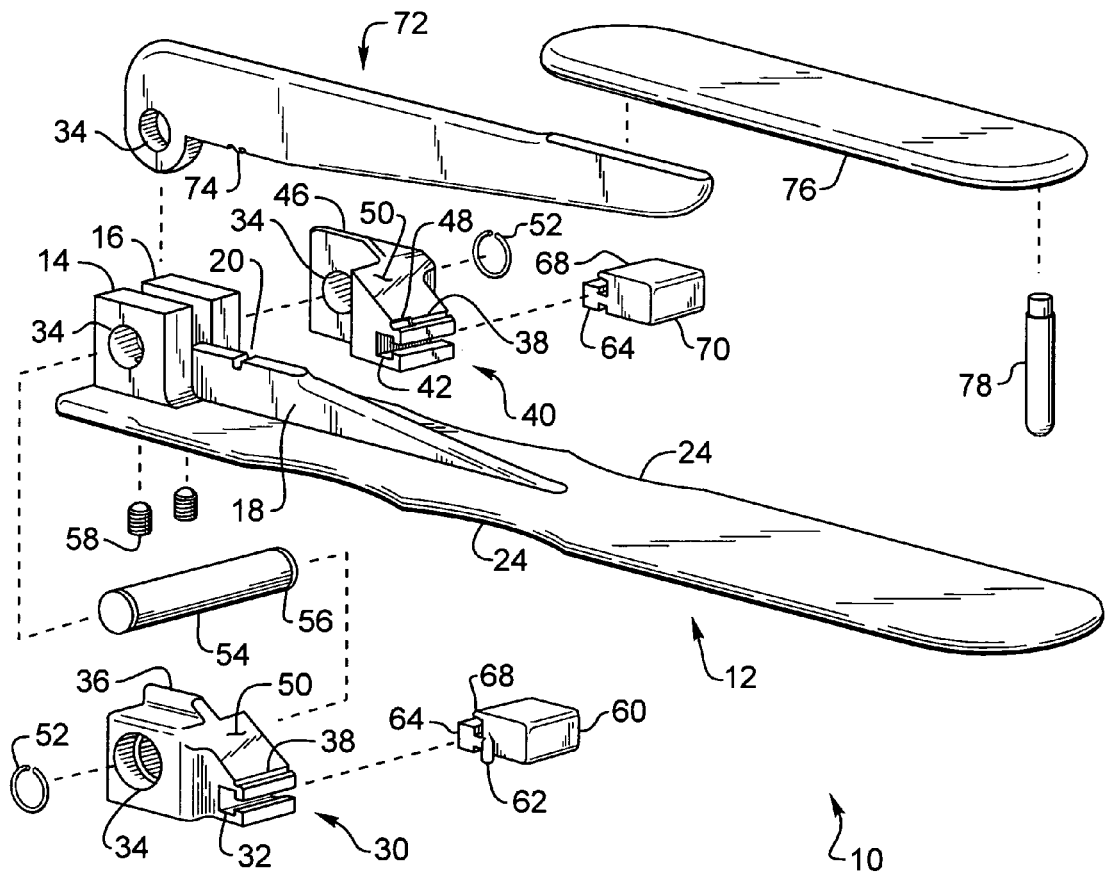
FIG. 3 is an illustration of an expanded perspective view of the crimping device 10 in accordance with the exemplary embodiment of the invention.

FIG. 3 is an illustration of an expanded perspective view of the crimping device 10 in accordance with the exemplary embodiment of the invention. The crimp lever 72 comprises a bore 34 for receiving the pin 54 and adjacent side broad surfaces to fit within the slot between a wire boss 14 and a connector boss 16 of the base 12. A paddle 76 is welded to the lever 72 where the paddle 76 includes a force limiter 78 that limits the minimum distance between the paddle and the base 12. In addition to the anvil boss 18 and the crimp anvil 20, the base 12 includes gripping aids 24 formed by removing a portion of the base 12. Both the wire boss 14 and the connector boss 16 have coaxial bores 34 for receiving a pin 54. The pin 54 is affixed in bores 34 of the bosses by setscrews 58. Each end of the pin 54 has a semi-toroidal groove 56 to accept a split retaining ring 52 made of round stainless steel wire. In some circumstances, a lanced pin (not shown) is pressed only into the bores 34 of wire boss 14 and connector boss 16 allowing the setscrews 58 to be eliminated while other components are free to move on the pin 54.

The wire holder 30 in the exemplary embodiment is slideably affixed by the bore 34 on pin 54. The travel of the wire holder 30 is bounded by the broad face of the wire boss 14 in the inward direction (toward the connector holder 40) and by a retaining ring 52 in the outward direction (away from the connector holder 40). In some circumstances, the bore 34 and the pin 54 are lubricated with a suitable lubricants such as Krytox® perfluorinated grease (Krytox is a registered trademark of E. I. DuPont De Nemours and Company Corporation). The wire holder 30 includes a protruding finger tab 36 to aid in positioning the wire holder 30 in the exemplary embodiment. A mortise 32 in the wire holder 30 is configured to receive the wire retainer 60. The flexible wire retainer 60, semi-cylindrical medical wire groove 38, and a ramp 50 facilitate insertion of the medical wire 110 as discussed below in further detail. The wire retainer 60 is made from rubber in the exemplary embodiment and includes a tenon 64 to fit the mortise 32, a detent 62, and a nose 68 to secure the medical wire 110.

The connector holder 40 is slideably affixed by bore 34 on pin 54. The travel of the connector holder 40 is bounded by the broad face of the connector boss 16 in the inward direction (toward the wire holder 30), and by retaining ring 52 in the outward direction (away from the wire holder 30). In some circumstances, the bore 34 and the pin 54 are lubricated with a suitable lubricant such as Krytox perfluorinated grease. The connector holder 40 includes a protruding pull tab 46 in the exemplary embodiment to aid in positioning the connector holder 40. The connector holder includes a mortise 42 configured to receive the connector retainer 70. The connector retainer 70, a semi-cylindrical tube-and-lead groove 48, and a ramp 50 facilitate insertion of the crimp connector 100 as described in further detail below. The connector retainer 70 has a tenon 64 to fit mortise 42, a detent 62 (not visible), and a nose 68 to secure the crimp connector 100.

In the exemplary embodiment, the base 12, the lever 72, the pin 54, and the retaining rings 52 are made of corrosion resistant metal or alloy such as 17-4 PH stainless steel. The wire holder 30 and the connector holder 40 are made of machined or molded polymer such as polyarylethersulfone. The wire retainer 60 and the connector retainer 70 are made of hydrolysis- and depolymerization-resistant elastomer, such as silicone rubber. An example of a suitable hardness of the retainers 60, 70 is approximately 79 on the Shore A scale.

Figure 4:
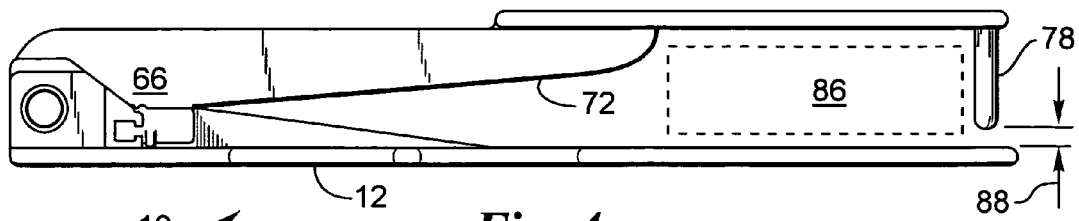
FIG. 4 is an illustration of a side view of the exemplary crimping device in the closed position.

FIG. 4 is an illustration of a side view of the exemplary crimping device 10 in the closed position. In the closed position, a gap 88 remains between the force limiter 78 and the base 12, where the gap 88 allows over-travel and tactile feedback during crimping. The protected storage area 86 is indicated by dashed lines.

Figure 5:
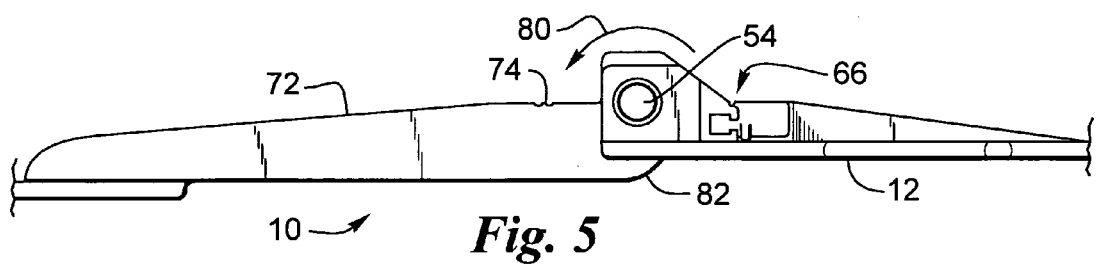
FIG. 5 is an illustration of a portion side view of the exemplary crimping device 10 in the open position.

FIG. 5 is an illustration of a portion side view of the exemplary crimping device 10 in the open position. In the open position, the crimp lever 72 is rotated in direction 80 about the pin 54 in order to provide the greatest possible access to the crimping area 66 and holders 30, 40. Further rotation of the lever 72 is stopped by contact between the end of the lever 72 and the slot in base 12 (not visible). Any pinching during the opening process is prevented by a protruding portion 82 of lever 72. The open position also provides access for inspecting the crimping die 74 and any items in the storage area 86.

Figure 6:
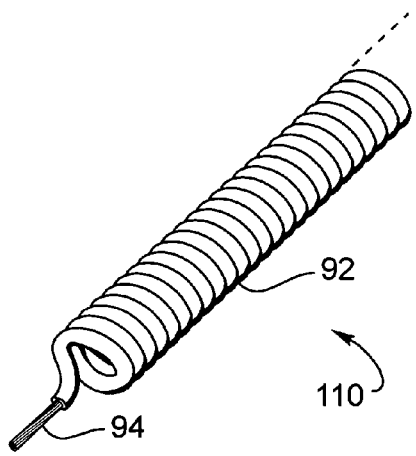
FIG. 6 is an illustration of a perspective view of a medical wire where the medical wire is a monofilar implantable lead.
Figure 7:
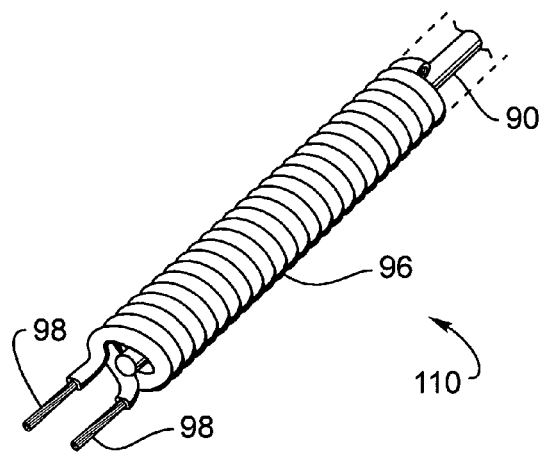
FIG. 7 is an illustration of a perspective view of a medical wire where the medical wire is a Peterson lead.

The medical wire 110 may include any of several types of medical wires, leads or other conductors. In the exemplary embodiment, the medical wire 110 is any of several types of medical wires 110 having conductors covered by insulation and that may be implanted into living tissue. FIG. 6 and FIG. 7 include illustrations of examples of medical wires 110 suitable for use with the exemplary embodiment of the invention. Other medical wires 110 and leads may be used in some circumstances.

FIG. 6 is an illustration of a perspective view of a medical wire 110 where the medical wire 110 is a monofilar implantable lead 92. The monofilar implantable lead 92 includes stranded metal conductors 94 (shown stripped only for clarity) that are sheathed in a perfluorinated polymer electrical insulation. Often referred to as a Shimada lead, the monofilar implantable lead 92 includes a coil that is 0.51 mm in diameter and has 28 coils per cm. The stranded metal conductors 94 are wires having a diameter of 44 µm, made of 316L (low carbon) stainless steel.

FIG. 7 is an illustration of a perspective view of a medical wire 110 where the medical wire 110 is a Peterson lead 96. The exemplary Peterson lead 96 has a diameter of 0.61 mm and bifilar windings of 30 coils per cm. The conductors 98 (shown stripped only for clarity) are wires having a diameter of 44 µm, made of 316L (low carbon) stainless steel. The conductors 98 are arranged in two nested groups with opposite slow twist. The wire bundle is encapsulated in a transparent, perfluorinated polymer. A core 90 of high strength polymer monofilament runs the entire length of the lead to insure stability.

Figure 8:
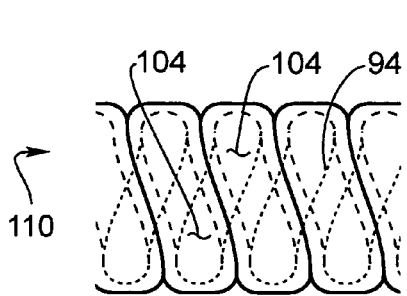
FIG. 8 is an illustration of a partial plan view of the medical wire of FIG. 6.

FIG. 8 is an illustration of a partial plan view of the medical wire 110 of FIG. 6. In FIG. 8, the stranded metal conductors 94 are outlined by dashed lines as they follow a helical path, the coarse dash indicate portions lying below the center plane, and the fine dashed lines define those portions above the center plane. When the monofilar implantable lead 92 (110) is crimped (into the plane of FIG. 8) there are crossing areas 104 in which the over and under portions of the stranded metal conductors 94 overlap and cross. During crimping, the stranded metal conductors 94 become thinner and wider until overlapping and crossing areas 104 constitute the preponderance of the area within the footprint of the crimp. The overlapping and crossing character of coiled leads is discussed in further detail below with discussion of the crimping process.

Figure 9:
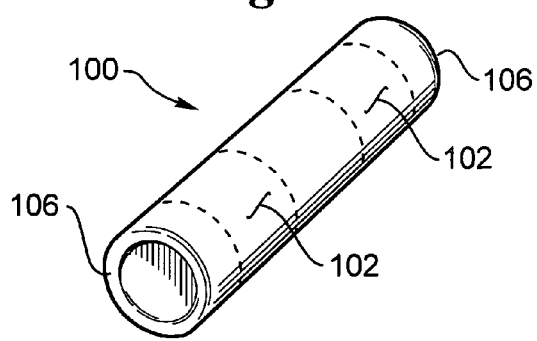
FIG. 9 is an illustration of a perspective view of a crimp connector in accordance with the exemplary embodiment of the invention.

FIG. 9 is an illustration of a perspective view of a crimp connector 100 in accordance with the exemplary embodiment of the invention. The crimp connector 100 may have any of several configurations, shapes and sizes. An example of a suitable crimp connector 100 is a barrel type connector formed by cutting a segment of drawn seamless metal tubing. Suitable crimp connectors 100 for use with Shimada and Peterson medical wires are made of 316L stainless steel to insure electrochemical compatibility. The exemplary crimp connector 100 has a diameter of approximately 1.0 mm and a bore slightly larger than the medical wires 110 to be crimped. End edges 106 are rounded to protect the medical wire 110 and any covering applied to the crimp connector 100 after crimping. In the exemplar embodiment, the inner edges are rounded to facilitate inserting the ends of the medical wire 110. Two crimp zones 102 are indicated by circumferential dashed lines in FIG. 9. The exemplary crimp connector 100 is symmetric about its axis to simplify handling and positioning.

Figure 10:
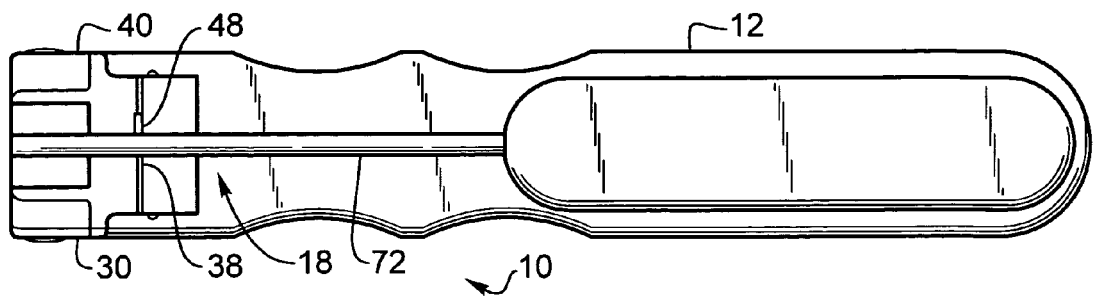
FIG. 10 is an illustration of a top view of the exemplary crimping device in the closed position.

FIG. 10 is an illustration of a top view of the exemplary crimping device 10 in the closed position. In the closed position, the crimp lever 72 is closed on the base 12, the wire holder 30 is closed so that wire groove 38 abuts the anvil boss 18, and the connector holder 40 is closed so that the tube-and-lead groove 48 abuts the anvil boss 18.

Figure 11:
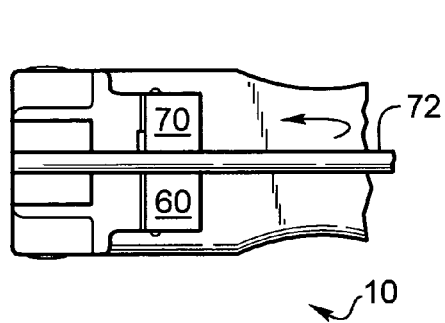
FIGS. 11 through 16 are illustrations of top views of a portion of the exemplary crimping device during the crimping process.

FIGS. 11 through 16 are illustrations of top views of a portion of the exemplary crimping device 10 during the crimping process. FIG. 11 is an illustration of a top view of the crimping device 10 as the crimping device 10 is opened from a closed position to the open position. The crimping device 10 is opened by rotating the crimp lever 72 in the direction of the arrow.

Figure 12:
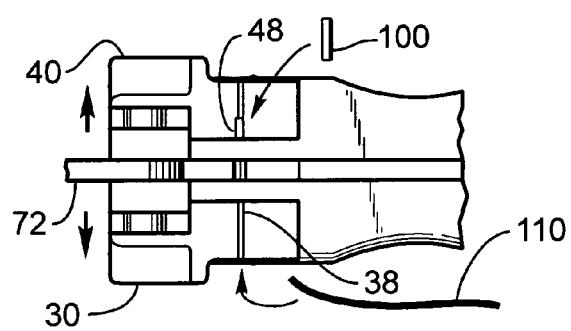

FIG. 12 is an illustration of a top view of the crimping device 10 as the wire holder 30 and the connector holder 40 are opened. The wire holder 30 and connector holder 40 are moved in an outward direction as indicated by straight arrows. The crimp connector 100 is placed in the tube-and-lead groove 48 and the medical wire 110 is placed in the wire groove 38 to secure the crimp connector 100 and the medical wire 110 within the holders 30, 40.

Figure 13:
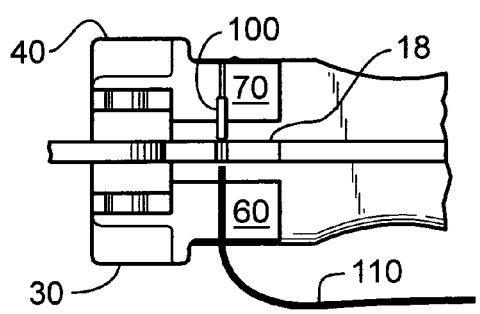

FIG. 13 is an illustration of a top view of the crimping device 10 with the crimp connector 100 and the medical wire 110 secured in the connector holder 40 and the wire holder 30, respectively. The crimp connector 100 and medical wire 110 are held in the predetermined axial locations by the respective connector retainer 70 and the wire retainer 60 as discussed in further detail below. The edge of the crimp connector 100 abuts the anvil boss 18. The axial location of the crimp connector 100 is determined in part by the position of the connector holder 40 and in part by the edge of the wire groove 38. The axial location of the medical wire 110 is determined in part by the position of the wire holder 30 and by observing that the end of the medical wire 110 abuts the anvil boss 18 during insertion of the medical wire 110. The lateral positions of all parts are predetermined and controlled by the locations of the base 12, the pin 54, and the grooves 38, 48 relative to the nominal center of the crimper assembly 6.

Figure 14:
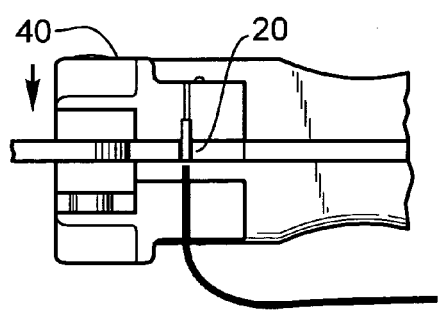

FIG. 14 is an illustration of a top view of the crimping device 10 as the connector holder 40 is moved from the open position to the closed position. The connector holder 40 is moved inward, as indicated by the arrow, until the inner half of the crimp connector 100 is accurately positioned over the crimp anvil 20.

Figure 15:
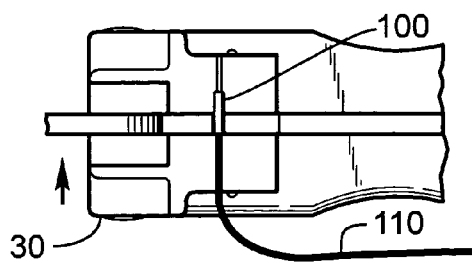

FIG. 15 is an illustration of a top view of the crimping device 10 as the wire holder 30 is moved from the open position to the closed position. The wire holder 30 is moved inward as indicated by the arrow in order to slip the end of the medical wire 110 into the open end of the crimp connector 100. As the wire holder 30 is fully closed, the end of the medical wire 110 is positioned just short of the center plane of the crimp connector 100. In the exemplary embodiment, a medical wire 110 or lead resides in each half of the crimp connector 100 in a completed crimp connection. Accordingly, predetermined axial repositioning of leads precludes a faulty crimp by dint of under-insertion, and precludes an impossible or faulty splice due to over-insertion. The crimp lever 72 is closed and the paddle pressed toward the base 12 until gap 88 between force limiter 78 and base 12 vanishes, and contact is felt by the operator. The gap 88 allows for over-travel and tactile feedback; whereas the abutting surfaces of the lever 72 and the anvil boss 18 control the actual crimping force.

Figure 16:
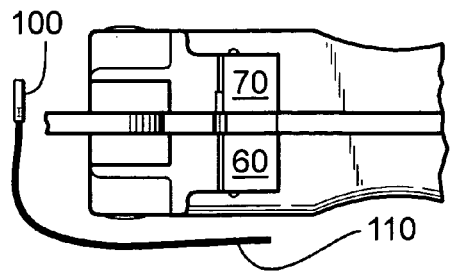

FIG. 16 is an illustration of a top view of the exemplary crimping device 10 in the open position and completed crimped assembly released from the crimping device 10. The crimped assembly includes the crimp connector 100, the medical wire 110 and, in some circumstances, a biomedical device. The crimped assembly is released by applying a downward fingertip pressure to the retainers 60, 70 and gently wiggling the medical wire 110 in order to release it without applying undesirable tension to the lead.

FIG. 17 through FIG. 20 are illustrations of a sequence of side elevation portion views of the wire holder 30 during an exemplary process of inserting the medical wire 110 into the wire holder 30. In the exemplary embodiment of the invention, a ramp 49 of the wire holder 30, in combination with the top surface of the wire retainer 60, forms a shallow valley configured to fit the fingertip 108 of a surgeon or other crimp device operator.

Figure 17:
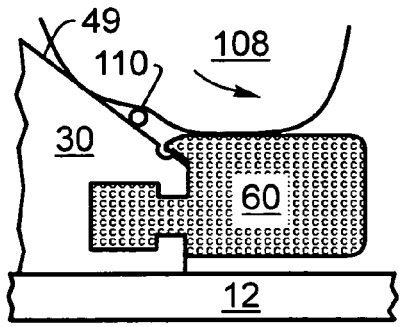
FIGS. 17 through 20 are illustrations of a sequence of side elevation portion views of the wire holder during an exemplary process of inserting the medical wire into the wire holder.

FIG. 17 is an illustration of a side elevation portion view of the wire holder 30 as the operator slides the medical wire 110 down the ramp 49. The operator slides and rotates a fingertip 108 in the direction of the arrow while pressing the medical wire 110 against the ramp 49 to move the medical wire 110 down the ramp 50. In most circumstances, the surgeon will feel, but not see, medical wire 110 slide down the ramp 49.

Figure 18:
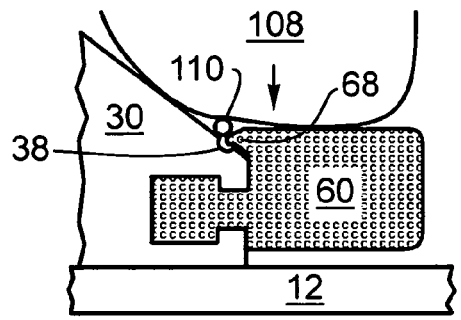

FIG. 18 is an illustration of a side elevation portion view of the wire holder 30 as the operator presses the medical wire 110 into the wire groove 38. The operator uses the fingertip 108 to press the medical wire 110 in the direction of the arrow while placing increasing pressure on the top surface of wire retainer 60. The operator, in most situations, will not see the medical wire 110 come in contact with the nose 68 of the wire retainer 60. In most circumstances, the operator will feel, and possibly hear, the medical wire 110 come in contact with the nose 68 of the wire retainer 60. The wire groove 38 is partially closed by the nose of the wire retainer 60.

Figure 19:
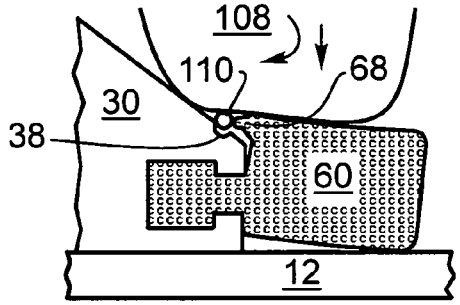

FIG. 19 is an illustration of a side elevation view of the wire holder 30 as the operator continues to press the medical wire 110 into the wire groove 38. The fingertip 108 is continually rolled in the direction of the curved arrow while simultaneously and progressively increasing the downward pressure (straight arrow) on the wire retainer 60 until the wire retainer 60 deforms enough to move the nose 68 away from the wire groove 38 to admit the medical wire 110 into the wire groove 38 of wire holder 30. In most circumstances, the operator will feel and hear, but not see, the snap of the medical wire into the wire groove 38.

Figure 20:
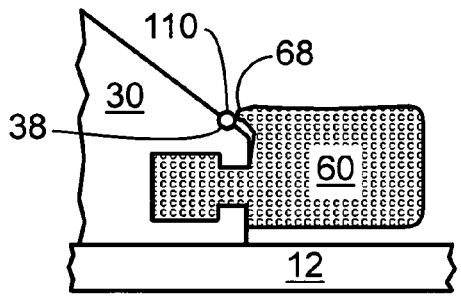

FIG. 20 is an illustration of a side elevation view of the wire holder 30 where the medical wire 110 is secured in the wire groove 38 by the wire retainer 60. After the fingertip 108 is rolled to the left to remove some of the downward pressure on the wire retainer 60, the nose 68 of the wire retainer 60 firmly axially restrains the medical wire 110 in the wire groove 38. The operator visually determines that the end of the medical wire 110 abuts the face of the anvil boss 18. If the end of the medical wire 110 is not in the abutting position, the medical wire 110 is adjusted using the fingertip 108. In most circumstances, some squirming of the fingertip 108 will move the medical wire 110 to the desired position.

FIGS. 21 through 24 are illustrations of a sequence of side elevation portion views of the connector holder 40 during an exemplary sequence of inserting the crimp connector 100 into the connector holder 40. A ramp 50 of the connector holder 40, in combination with the top surface of connector retainer 70, forms a shallow valley configured to fit the gloved fingertip 108 of the surgeon.

Figure 21:
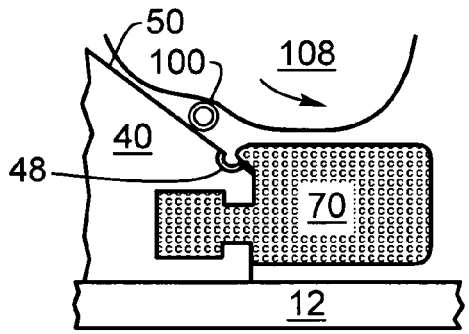
FIGS. 21 through 24 are illustrations of a sequence of side elevation portion views of the connector holder during an exemplary sequence of inserting the crimp connector into the connector holder.

FIG. 21 is an illustration of a side elevation portion view of the connector holder 40 as the operator slides the crimp connector 100 into the groove 48. The surgeon presses crimp connector 100 against ramp 50 while sliding and rotating a gloved finger 108 in the direction of the arrow. The surgeon will feel the sliding of the crimp connector 100 in most circumstances.

Figure 22:
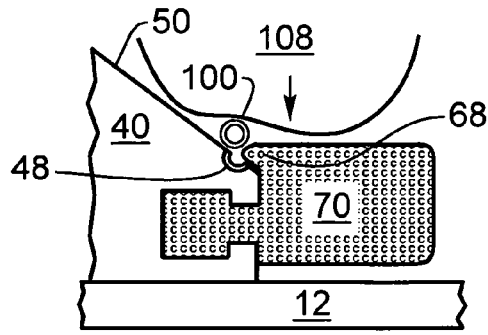

FIG. 22 is an illustration of a side elevation portion view of the connector holder 40 as the operator presses the crimp connector 100 into the tube-and-lead groove 48. The fingertip 108 presses the crimp connector 100 in the direction of the arrow while placing increasing pressure on the top surface of connector retainer 70. In most circumstances, the operator will feel and possibly hear the crimp connector 100 come in contact with the nose 68 of connector retainer 70. The groove 48 is partially closed by the nose 68 of the connector retainer 70.

Figure 23:
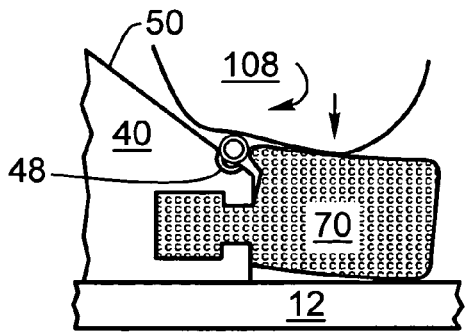

FIG. 23 is an illustration of a side elevation portion view of the connector holder 40 as the fingertip 108 further guides the crimp connector 100 into the tube-and-lead groove 48. The fingertip 108 continually rolls in the direction of the curved arrow while simultaneously and progressively increasing the downward pressure (straight arrow) on the connector retainer 70 until it deforms enough to admit the crimp connector 100 into the groove 48. The surgeon will feel and hear the snap of the crimp connector 100 into the groove 48 in most circumstances.

Figure 24:
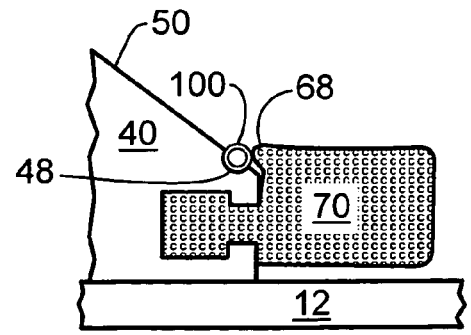

FIG. 24 is an illustration of a side elevation portion view of the connector holder 40 where the crimp connector 100 is secured in the groove 48 by the connector retainer 70. The fingertip is rolled to the left to remove the downward pressure on the connector retainer 70 such that the nose 68 of the connector retainer 70 firmly retains the crimp connector 100 in the groove 48. The operator visually inspects the crimp connector 100 to verify that the inner end (open end) of the crimp connector 100 abuts the face of the anvil boss 18 and that the outer end of the tube is fully seated in the end of the groove 48.

Figure 25:
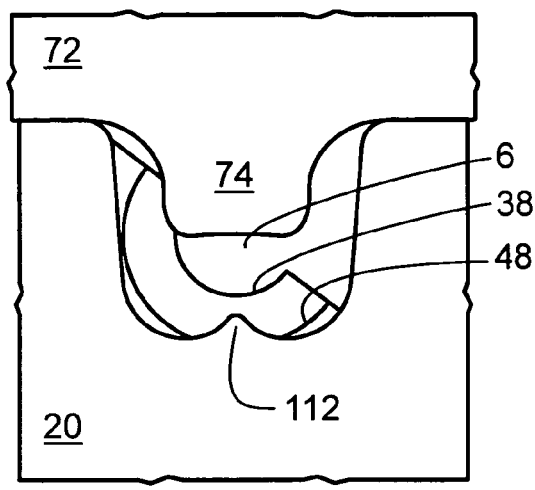
FIG. 25 is an illustration of a side elevation portion view of crimp die closed on the anvil with the wire holder omitted for clarity.

FIG. 25 is an illustration of a side elevation portion view of crimping die 74 closed on the anvil 20 with the wire holder 30 removed for clarity. In the exemplary embodiment, the anvil 20 has a penetrator 112 that facilitates the crimping process as described below in further detail. The side walls of the anvil cavity diverge from the center plane to reduce wedging of the crimped connector 100 and allow the crimp connector 100 to be released without applying unwanted tension to the medical wire 110. As illustrated in FIG. 25, the wire groove 38 is coaxial with the tube-and-lead groove 48 in the exemplary embodiment. The lateral positions of the crimp connector 100 and medical wire 110 are determined by the relative locations of the wire holder 30 and connector holder 40 and their respective grooves 38, 48. The wire holder 30 and connector holder 40 slide on the pin 54 but are restricted from rotating about the axis of the pin 54 in order to provide precise spatial alignment of the medical wire 110 and the crimp connector 100 relative to the nominal center of the crimper assembly 6. The inner planar face of the connector holder 40 slides along the proximate planar face of the connector boss 16 of the base 12 and the inner planar face of the wire holder 30 slides along the proximate planar face of the wire boss 14, thereby constraining the holder motion to linear translation. In some circumstances, the sliding proximate faces of the wire holder 30 and connector holder 40 and the wire bosses 14 and connector boss 16 are lubricated with Krytox perfluorinated grease.

Figure 26:
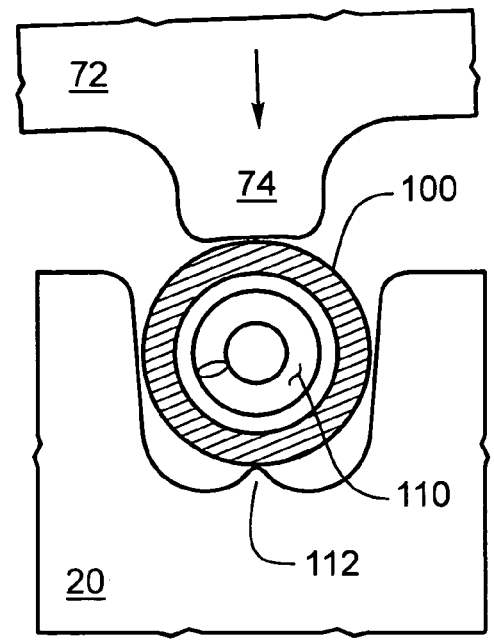
FIGS. 26, 27, and 28 are illustrations of a sequence of side elevation portion views of the crimp die and the crimp anvil during the crimping process.
Figure 27:
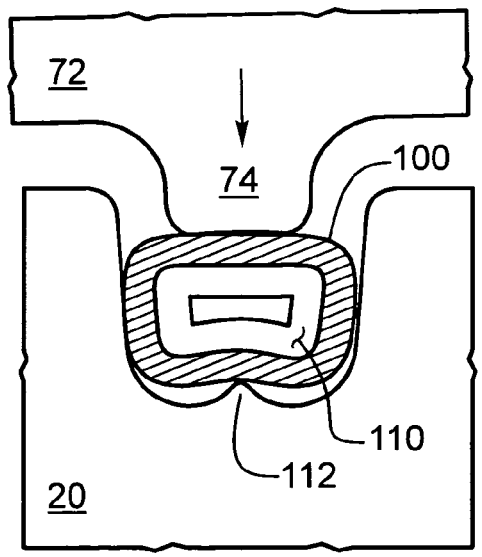
Figure 28:
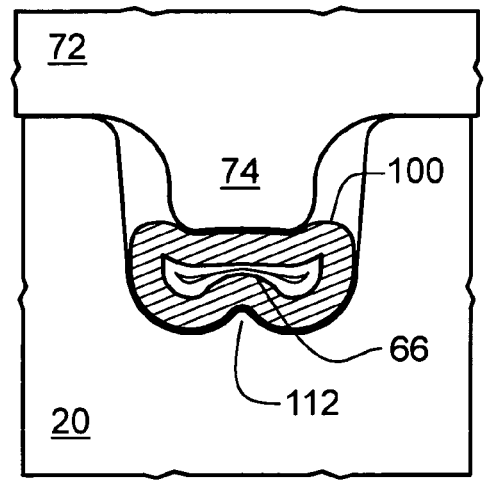

FIG. 26 through FIG. 28 are illustrations of a sequence of side elevation portion views of the crimping die 74 and the anvil 20 during the crimping process. The medical wire 110 within the crimp connector 100 is squeezed between the crimping die 74 and the anvil 20 as the crimping die 74 is moved toward the anvil 20. Although the exemplary crimping device 10 is a hand tool that is manually operated, the crimping device may include other mechanisms for forcing the crimping die 74 toward the anvil 20. A pneumatic mechanism, for example, may be used to perform or to assist the operator in activating the crimper assembly 6 in some circumstances.

FIG. 26 is a side elevation portion view of the crimper assembly 6 as the crimping die 74 contacts the crimp connector 100. The crimping die 74 begins a downward stroke in the direction of the arrow as the lever 72 is moved toward the base 12.

FIG. 27 is a side elevation portion view of the crimper assembly 6 as the crimp connector 100 is deformed. The crimping die 74 is completing half of the downward crimping stroke and is flattening the top surface of crimp connector 100. The penetrator 112 has begun to deform the bottom surface of the crimp connector 100 and the medical wire 110 is partly compressed.

FIG. 28 is a side elevation portion view of the crimper assembly 6 as the crimping die 74 has reached the maximum travel toward the anvil 20. The bottom surface of the crimp lever 72 abuts the top surface of anvil 20, thereby completing the crimping stroke. The penetrator 112 forms an axial rounded ridge of a predefined radius in the inner wall of the crimp connector 100. The distance from the ridge crest to the ceiling of crimp connector 100 is configured to displace the electrical insulation of the medical wire 110 in order to bring the conductors in contact with each other and with the inner walls of crimp connector 100 to form an electrical and mechanical connection. During crimping, the stranded conductors are spread laterally and both the insulation and the portion of the crimp connector 100 in the crimping area 66 are displaced axially outward (stretched). Stripping the electrical insulation from the end of the medical wire 110 is not required, and would likely interfere with achieving an optimum final crimp geometry. In some circumstances, the medical wire 110 is crimped while wetted or flooded with uncured silicone elastomer in order to inhibit body electrolyte permeation.

Figure 29:
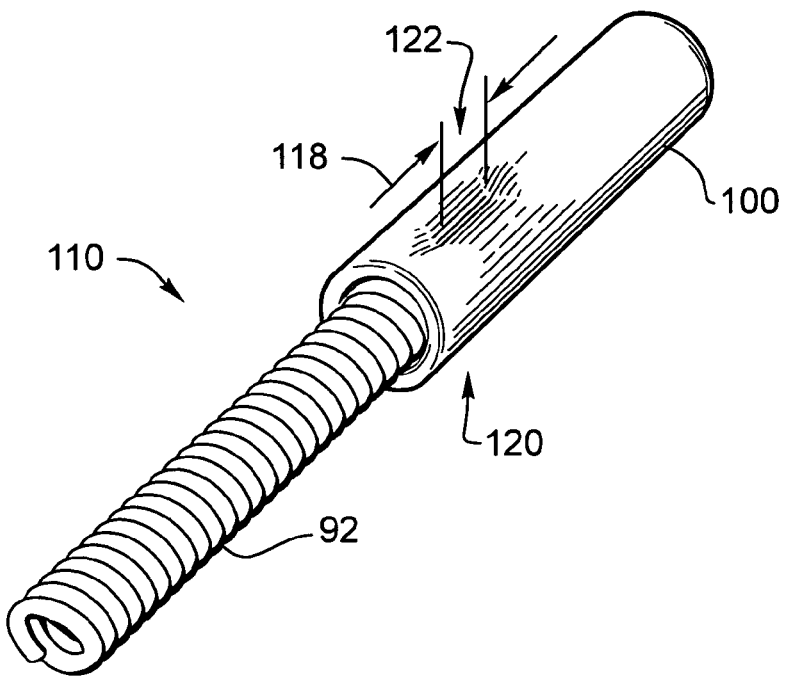
FIG. 29 is an illustration of a perspective portion view of a crimp connector crimped to a medical wire where the medical wire is a monofilar implantable lead.

FIG. 29 is an illustration of a perspective portion view of a crimp connector 100 crimped to a medical wire 110 where the medical wire 110 is a monofilar implantable lead 92. The anvil crimp portion 122 of the crimp has an axial length 118 that is approximately equal to the diameter of the crimp connector 100 in the exemplary embodiment. The die crimp portion 120 of the crimp is located on the opposite (not visible) side of crimp connector 100. The transition from the fully crimped area to the non-deformed portions of the crimp connector 100 is symmetric.

Figure 30:
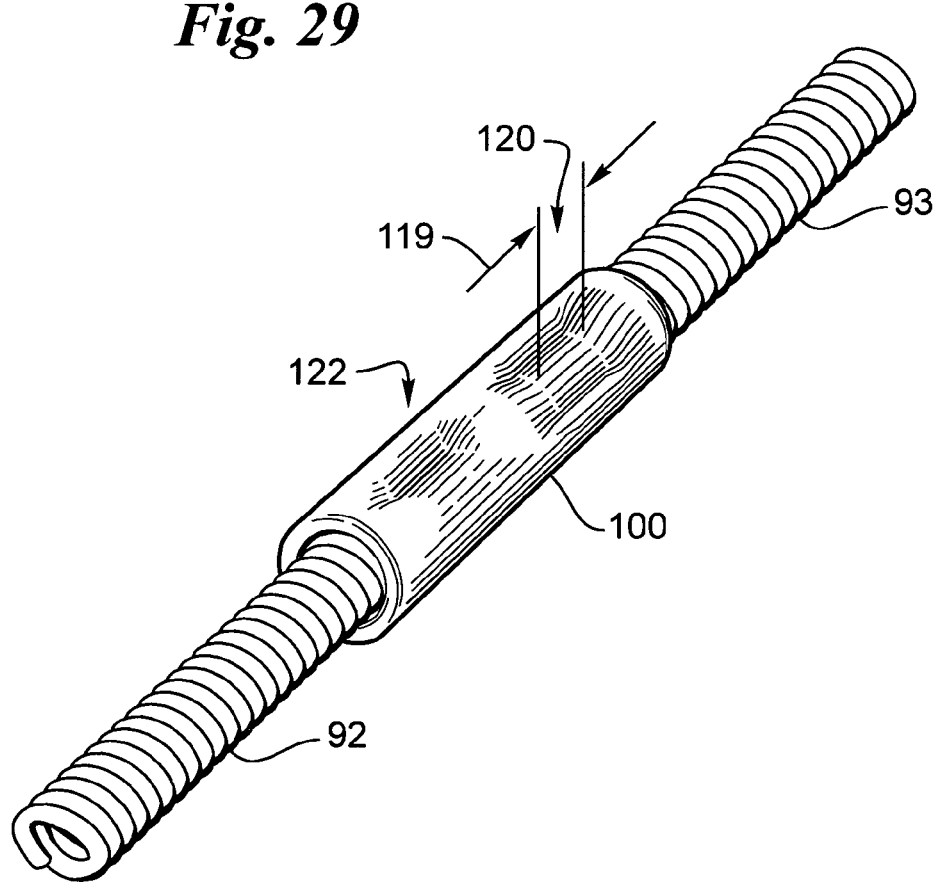
FIG. 30 is an illustration of a perspective portion view of a completed splice of two medical wires where the monofilar implantable lead is connected to a second monofilar implantable lead by a crimp connector.

FIG. 30 is an illustration of a perspective portion view of a completed splice of two medical wires 110 where the monofilar implantable lead 92 is connected to a second monofilar implantable lead 93 by a crimp connector 100. The crimp connector 100 has the anvil crimp portion 122 of the first crimp and a die crimp portion 120 of a second crimp having an axial length 119 approximately equal to the diameter of crimp connector 100. The axial length 119 is equal to the axial length 118 in the exemplary embodiment. In some circumstances, the axial lengths 118, 119 may be different. Although the die crimp portion 120 and anvil crimp portion 122 may be collinear in some situations, they need not be collinear since the wire holder 30 and connector holder 40 do not direct the medical wires 110 and the crimp connector 100 in any particular orientation. Where the medical wires 110 are Peterson leads, the core of the Peterson lead is displaced along with the electrical insulation resulting in a similar crimp or splice as a Shimada lead. The core 90 is also mechanically anchored by the crimp where a Peterson lead is used.

In some circumstances, the second monofilar implantable lead 93 is connected to a biomedical device such as a sensor, a stimulation electrode, a signal detection electrode, or an electronic module. The lead 93 is integrally constructed with a biomedical device in some situations.

Figure 31:
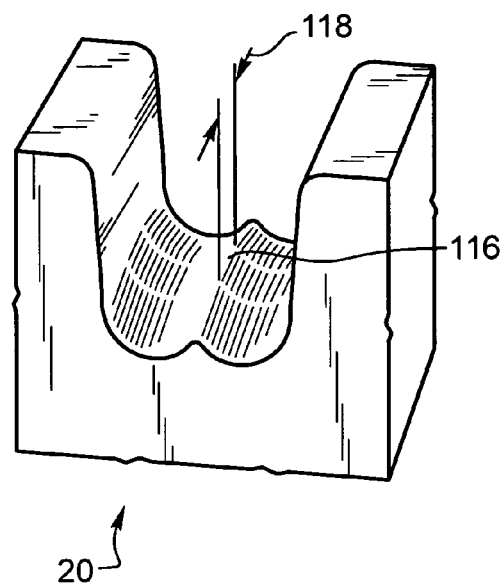
FIG. 31 is an illustration of a perspective portion view of the crimp anvil in accordance with the exemplary embodiment of the invention.

FIG. 31 is an illustration of a perspective portion view of the anvil 20 in accordance with the exemplary embodiment of the invention. The exemplary anvil 20 has a central crimp area 116 having an axial length 118 (relative to the crimp connector 100) that is approximately equal to the diameter of the crimp connector 100. On either side of the central crimp area 116, the topology of the anvil 20 is repeated, but angularly disposed to the central crimp area 116. The angle is predetermined to provide a smooth transition from central crimp area 116 to the undeformed portions of the crimp connector 100 and to retain concavity symmetrically about the central crimp area 116. An enlarged concavity (as opposed to an abrupt boundary of the central area) enhances the stored residual elastic energy that urges the crimp connector 100 inner walls toward the flattened conductive strands of the medical wire 110. An example of a suitable method of fabricating the predetermined transition includes using wire electric discharge machining (WEDM) where cutting forms the basic shape of the anvil 20. The base is rotated by the predetermined angle, and the anvil geometry (program) is retraced in order to bevel the edge of the otherwise abruptly truncated crimp area. The opposite edge of the crimp area is beveled using the negative of the predetermined angle. The WEDM is programmed to leave a central crimp area 116 having an axial length 118. An example of a suitable crimp anvil bevel angle lies in the range of 8 to 18 degrees.

Figure 32:
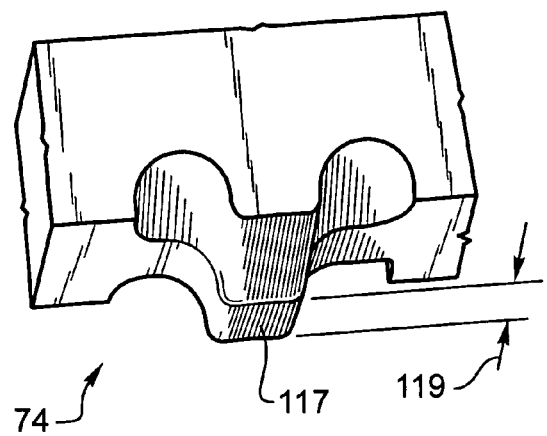
FIG. 32 is an illustration of a perspective portion view of the crimp die in accordance with the exemplary embodiment of the invention.

FIG. 32 is an illustration of a perspective portion view of the crimping die 74 in accordance with the exemplary embodiment of the invention. The exemplary crimping die 74 includes a central crimp portion 117 having an axial length 119. Although in some situations the central crimp area 116 and central crimp portion 117 may be different, the central crimp portion 117 is equal to the central crimp area 116 of the anvil 20 in the exemplary embodiment. A suitable method of forming the crimping die 74 includes using a beveling process similar to the process discussed above with reference to the anvil 20. An example of a suitable crimp die bevel angle lies in the range of 20 to 38 degrees. Tests of beveled crimps have determined that the bevel angle, in combination with the predetermined terminal distance between the crimping die 74 and the anvil 20, may be configured such that the electrical connection in the central crimp portion 117 of the crimp has a minimum electrical resistance while maximizing the mechanical retention of the medical wire 110 within the crimp connector 100. Tests have indicated that the mechanical retention due to the gripping of the medical wire 110 by the beveled portions of the crimp generally exceeds the strength of the medical wire 110. During tension testing, for example, the medical wire 110 breaks outside the crimp area. Further, testing has shown that an instrument having a preferred crimp configuration achieves excellent electrical and mechanical connections of medical wires 110 having dimensions and properties lying in the range between those of the Shimada lead (small) and the Peterson lead (large).

In some circumstances, bevels with two or more retraces of the WEDM profile program may be formed where each retrace is performed at a different prescribed angle in order to contour the bevel. The junction of the contour with the straight portion of the crimping die 74 or anvil 20 is angular in some situations and tangential in others.

Figure 33:
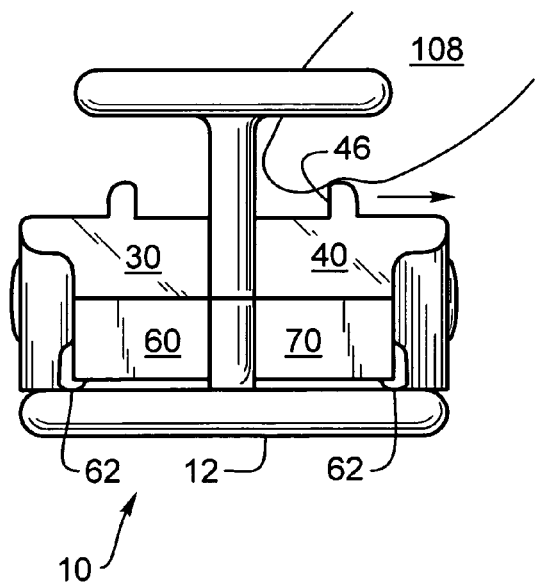
FIG. 33 is an illustration of an end elevation view of the crimping device with the holders in the closed position in accordance with the exemplary embodiment of the invention.
Figure 34:
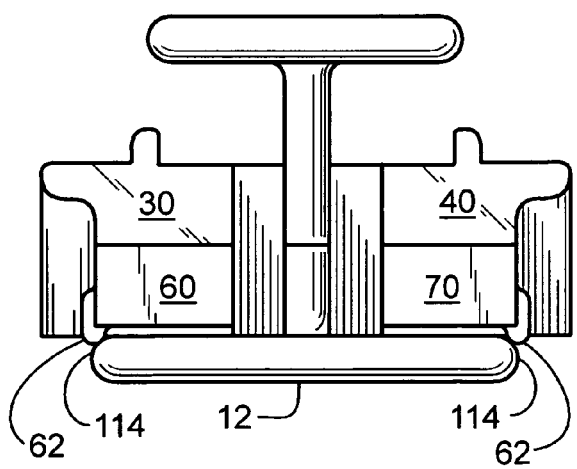
FIG. 34 is an illustration of an end elevation view of the crimping device with the holders in the open position in accordance with the exemplary embodiment of the invention.

FIG. 33 is an illustration of an end elevation view of the crimping device 10 in the closed position in accordance with the exemplary embodiment of the invention. The detents 62 of wire retainer 60 and connector retainer 70 are compressed by interference contact with the upper surface of the base 12. In some circumstances, the contacts are lubricated with Krytox perfluorinated grease to provide smooth sliding action. When the surgeon's fingertip 108 urges pull tab 46 in the direction of the arrow, the wire holder 30 and connector holder 40 slide smoothly to the open position as shown in FIG. 34. Just as a holder (30, 40) reaches the fully open position, the detent 62 begins to restore its uncompressed state. In the fully open position, the detent 62 retains a prescribed residual deformation that urges the contact between the detent 62 and the rounded shoulder 114 of the base 12 to keep the wire holder 30 and connector holder 40 in the fully open position in order to prevent inadvertent placement of the medical wire 110 or the crimp connector 100 in a less than optimum position.

Upon closing of the wire holder 30 and connector holder 40 tactile feedback informs the operator of the onset of closing by initially increasing resistance to sliding and indicating recompression of detents 62 in the exemplary embodiment. Visual, auditory, and tactile feedback further inform the operator that the closing strokes are completed and the wire holder 30 and connector holder 40 contact the respective proximate wire boss 14 and connector boss 16 of the base 12. In most situations, the trained operator or surgeon will watch the end of the medical wire 110 as it successfully enters the open end of the crimp connector 100.

After the initial portion of the holder (30, 40) closing stroke, recompression of the detents 62 urge an upward deformation of the retainers 60, 70 in order to increase the strength of their respective grips on the medical wire 110 and the crimp connector 100, which further reduces any tendency to inadvertently slide to less than an optimum position in the respective grooves 38, 48.

In some situations, the crimp connector 100 remains exposed when implanted. The crimp connector 100 forms an electrode in electrical contact with body tissue in order to stimulate a nerve or to detect nerve impulses. In some circumstances, an uncoated crimp connector 100 is coated with platinum or other substance known to achieve a more chemically inert and electrically less noisy contact. The interior of the crimp connector 100 may be protected with cured-in-place elastomer or other matter known to delay chemical attack by body electrolytes (wet crimping) as described above.

In a majority of applications, the desired function of the crimp is to extend the reach to electrical stimuli or detected signals at a location removed from the immediate vicinity of the crimped medical wire 110. As discussed below with reference to FIG. 39, a suitable technique for minimizing interaction with human tissue includes covering the completed splice with a segment of medical grade silicone rubber tubing (silicon rubber boot). The sleeve, tube, boot or molding tubular sleeve is slipped on the medical wire 110 before the crimp is completed. After completing the crimp the sleeve is pulled over crimp connector 100 and the silicon tubing is back-filled with uncured but activated elastomer. The sleeve ends are closed using sutures. Some of these steps are modified or omitted in some circumstances, for example, the backfilling step and the use of sutures is omitted in some situations. In addition to providing mechanical strain relief during normal body flexing, a sleeve protects the splice from chemical attack and electrically insulates the splice from body tissue. A spliced medical wire 110 insulated as described above facilitates maximum electrical conduction to and from an intended site.

In the exemplary embodiment, the materials used for constructing the crimping device 10 include materials known to be biocompatible with living tissue since many of the applications of the crimping device includes crimping medical wires 110 and crimp connectors 100 that are intended to be implanted, or re-implanted in living tissue. For example, Krytox perfluorinated grease is assumed to be biocompatible. The Food and Drug Administration does not require testing of the biocompatibility of Krytox because its similarity to other tested perfluorinated materials implies complete chemical inertness. Krytox is stable when subjected to repeated steam sterilization (autoclaving). Whereas Krytox is used in the interior portions of the exemplary crimping device 10, there is a remote possibility that the grease may be inadvertently transferred to implantable objects during surgery.

Further, Radel® R polyphenylsulfone (Radel is a registered trademark of Solvay S.A.) is a moldable plastic that has been successfully tested for biocompatibility in animals. Radel R resists hydrolysis, and retains dimensional stability after hundreds of autoclave cycles.

Stainless steel is notorious for galling when rubbed against itself, particularly when both parts are made of the same alloy. To prevent galling, modified tungsten disulfide powder is blasted onto at least one of the rubbing surfaces of stainless steel parts, then the excess powder is removed until further wiping removes no more material. Remnant tungsten disulfide is chemically bonded to the surface interstices of the stainless steel. The film strength of the lubricative treatment exceeds the strength of the stainless steel, resists hydrolysis, exposure to high temperature, and is stable when repeatedly sterilized in live steam. The application process is proprietary to Dicronite® Dry Lube, (Dicronite is a registered trademark of Lubrication Sciences, Inc.). Dicronite has been successfully tested for biocompatibility in animals.

Dicronite lubrication of surfaces sliding steel-on-steel may create microscopic particles of an alloy of stainless steel and tungsten disulfide, but these materials have successfully passed biocompatibility trials. In addition, subsequent lubrication with Krytox perfluorinated grease will entrap any microscopic particles, and the grease is known to be biomedically benign. Further, the configuration of the exemplary crimping device 10 minimizes the likelihood of the medical wire 110 or the crimp connector 100 from contacting the sliding surfaces. The anvil 20 and crimping die 74 surfaces that contact the crimp connector 100 are not treated with Dicronite in the exemplary embodiment.

An example of a suitable alloy for the metal portions of the exemplary crimping device 10 is 17-4 PH, which is known to resist corrosion in live steam (autoclaving), and may be hardened by heat treatment to approximately Rockwell 44 C in order to prolong the useful life of the crimping die 74 and the anvil 20. The crimping die 74 and anvil 20 are zone hardened (local heat treatment) in some circumstances. Steel parts are thoroughly cleaned, and then passivated in hot citric acid solution in order to remove the last vestiges of "free iron" that are suspected of initiating corrosion.

The exemplary crimping device 10 and method substantially enhances the convenience and speed with which a connection can be made thereby enabling a surgeon to easily replace a faulty connection with a new splice, extend an old lead, or replace an implanted component by cutting out the old splice or lead, and re-splicing. The length of the splice is relatively short, and very little of the length of a lead (medical wire 110) is lost when a splice is excised, because the leads may be cut immediately at the crimp connector 100 end.

Figure 35:
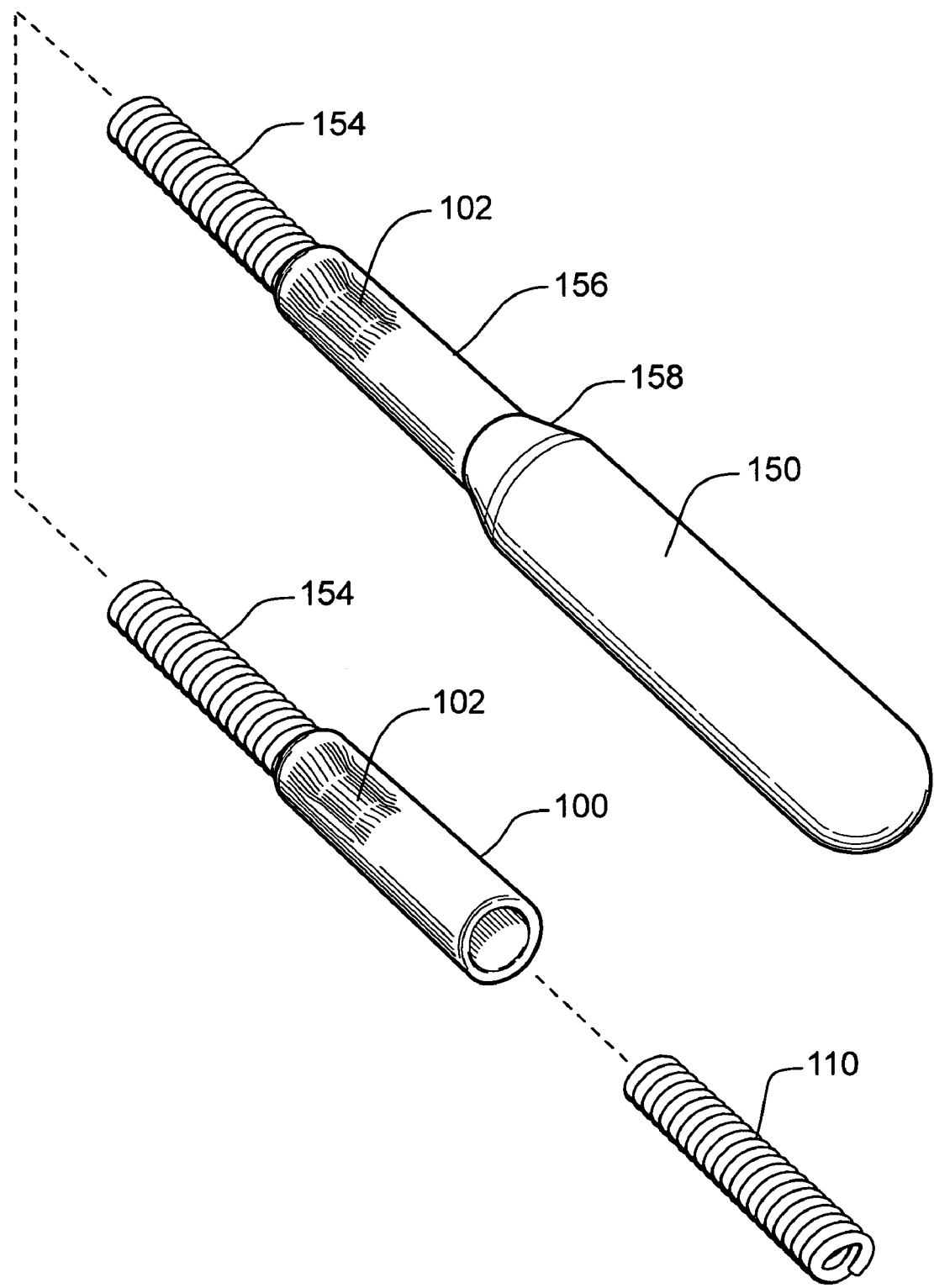
FIG. 35 is a perspective view of medical device assembly suitable for use with the exemplary embodiment of the invention.

FIG. 35 is a perspective view of medical device assembly suitable for use with the exemplary embodiment of the invention. As discussed above, common uses for implantable medical devices include implanting a medical device 150 for stimulating or sensing living tissue. Examples of implantable medical devices 150 include the Bion® medical devices (Bion is a registered trademark of Advanced Bionics Corporation) which may be used as sensors or as stimulators. As described above, it is often advantageous to connect a medical wire 110 to the medical device 150 to provide an electrical path between a target site and a suitable location within the host to implant the medical device 150. Typical implantation techniques often include connecting a medical device 150 to a medical wire 110 implanted in a host and subsequently implanting the medical device 150. The medical device 150, therefore, often is assembled as part of a medical device assembly that includes a short length of medical wire 154 that is terminated in a crimp connector 100. The medical wire 154 and connector 100 are often referred to as a "pigtail". The crimp connector 100 is connected to the implanted medical wire 110 at a sterile surgical site by the surgeon prior to implanting the medical device assembly.

The exemplary embodiment may be used with a variety of medical devices and medical devices 150 that are assembled in any of several ways. The exemplary medical device 150, however, is assembled under controlled conditions prior to use at the surgical site. A stub connector includes a stub head 158 and stub shaft (not shown). The stub head 158 is laser welded to the medical device 150 and a crimp connector 156 such a tube is pressed onto the stub shaft. The medical wire 154 is connected by crimping the crimp connector 156 to the medical wire 154 using crush-penetration and forcing a portion of the crimp connector 156 through the insulation of the medical wire 154 to make an electrical connection between the crimp connector 156 and the conductor of the medical wire 154. An example of a suitable material for the stub connector and crimp connector 156 is titanium alloy. The medical wires 110, 154 may include 316L stainless steel stranded wire insulated with PTFE insulation such as Teflon® (Teflon is a registered trademark of E. I. DuPont De Nemours and Company Corporation). The crimp connector 156 is crimped to the medical wire 110 by forming a crimp zone 102 such that the crimp zone 102 has a shape and dimensions adequate to accomplish crush-penetration through the insulation and make an electrical contact without damaging the inner stranded conductor of the medical wire 154. Those skilled in the art will recognize that the medical wire 154 may be any type of suitable medical wire or biomedical wire and may be referred to in the industry as a wire, medical wire, biomedical wire, lead or pigtail. Further, the medical wire 110 that is connected to the crimp connector 100 may be any type of suitable wire, medical wire or biomedical wire and may be implanted in a host, connected to other devices or connectors or may include only a section of wire. Those skilled in the art will recognize that the medical wire 110 may be referred to as a lead, wire, medical wire, extension wire, connection wire or by other terms.

Figure 36:
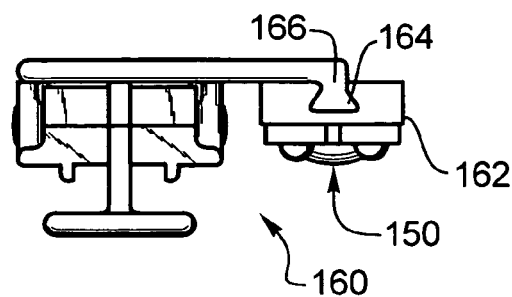
FIG. 36 is an illustration of a front view of a crimping device in accordance with second exemplary embodiment of the invention.

FIG. 36 is an illustration of a front view of a crimping device 160 in accordance with second exemplary embodiment of the invention. The crimping device 160 includes a medical device holder 162 for holding a medical device 150 while a medical wire 110 is crimped to the crimp connector 100 of the medical device assembly 150. Although in some circumstances the medical device holder 162 may be permanently attached to the crimping device 160, it is slideably attached to the crimping device 160 in the second exemplary embodiment.

Figure 37:
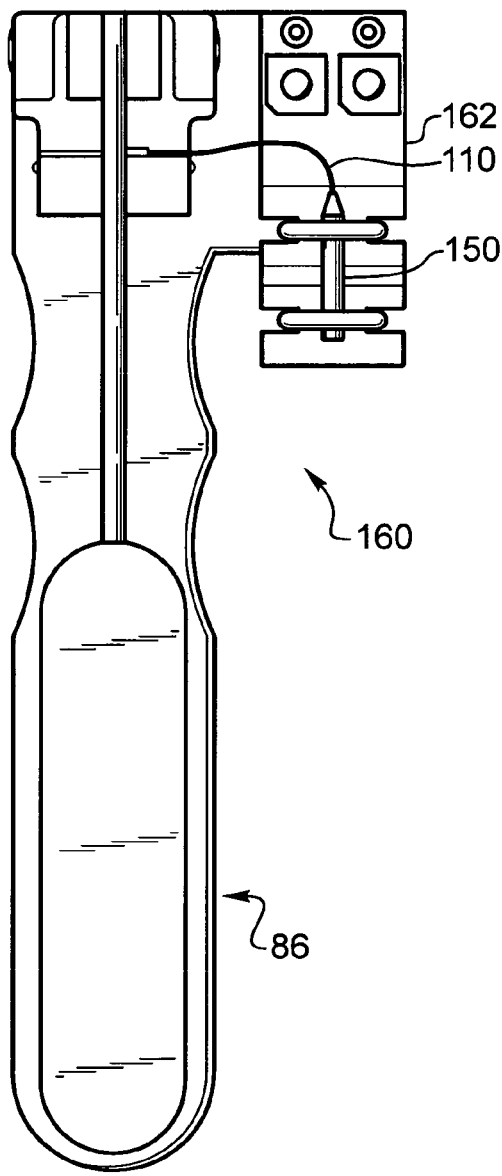
FIG. 37 is an illustration of a top view of the crimping device in accordance with the second exemplary embodiment showing the medical device holder attached to the crimping device.
Figure 38:
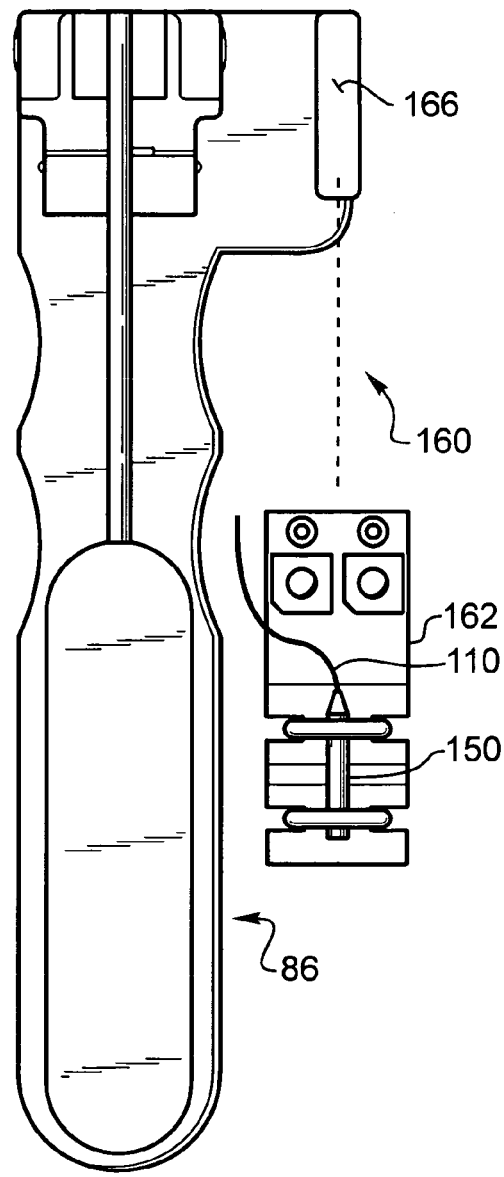
FIG. 38 is an illustration of a top view of the crimping device in accordance with the second exemplary embodiment showing the medical device holder unattached to the crimping device.

FIGS. 37 and 38 are top views of the crimping device 160 in accordance with the second exemplary embodiment where the medical device holder 162 is shown attached to the crimping device 160 in FIG. 37 and shown unattached in FIG. 38. The medical device holder 162 has a mortise 164 for accepting a tenon 166 of the crimping device 160. In many situations, the medical device assembly is secured within the medical device holder 162 prior to delivery at the surgical site. The surgeon slides the medical device holder 162 onto the crimping device 160 and secures the crimp connector 100 into the connector holder 40 as described above. After the medical wire 110 is secured in the medical wire holder 30 and the components are properly aligned, the crimp connector 100 of the medical device assembly is crimped to the medical wire 110 while the medical device 150 is held by the medical device holder 162. The device holder 162 may be positioned in any of several locations and orientations. For example, the device holder 162 may be positioned within the protected storage area 86 or underneath the crimper assembly 6 in some circumstances. The tenon 166, therefore, may be located within the protected storage area 86 (FIGS. 2 and 4) or in any other suitable location on the crimping device 10.

Figure 39:
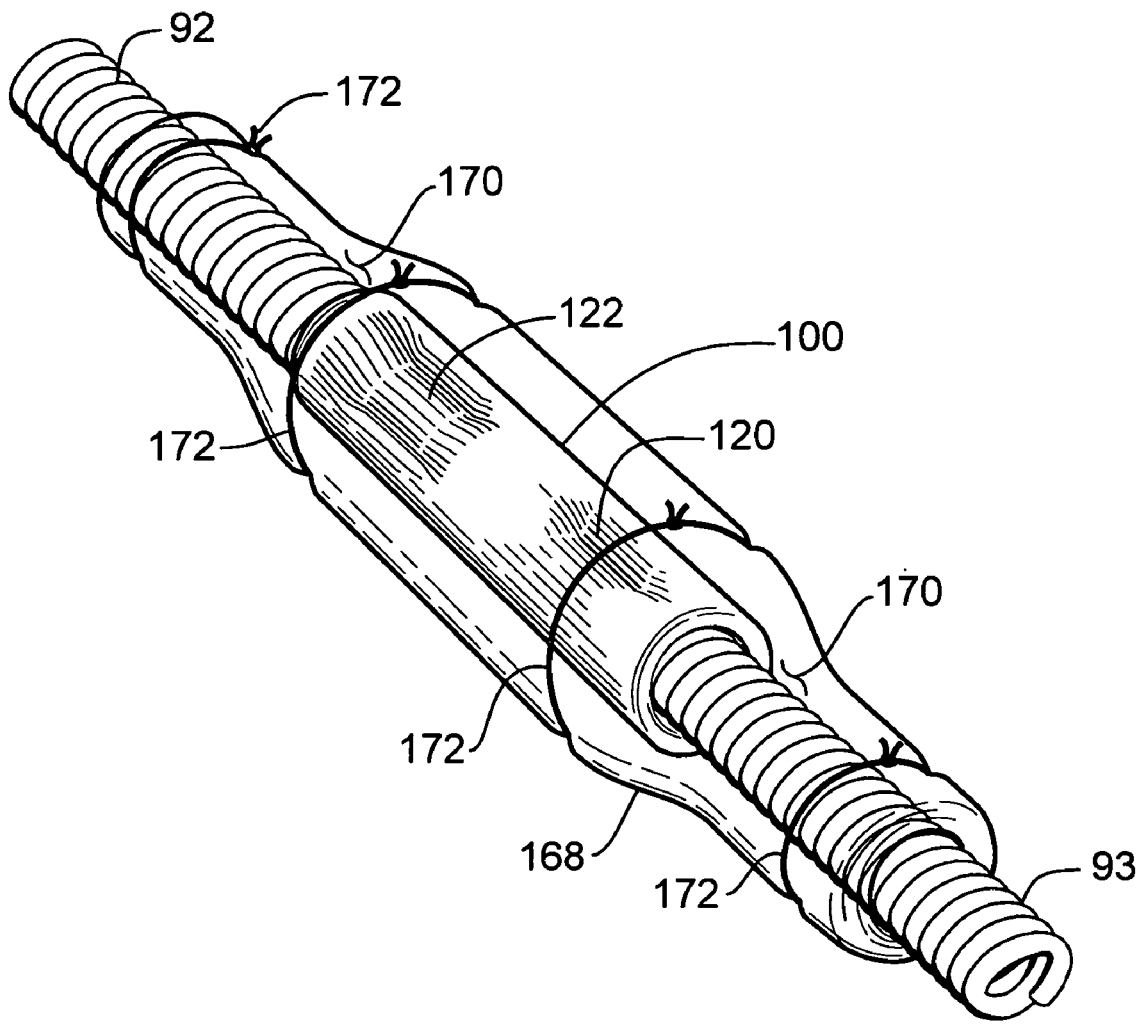
FIG. 39 is a perspective view of a completed crimp connection (splice) after crimping by a crimping device in accordance with the exemplary embodiment of the invention.

FIG. 39 is a perspective view of a completed crimp connection (splice) after crimping by a crimping device 10 in accordance with the exemplary embodiment of the invention. After the connection between the implanted monofilar implantable lead 92 and the second monofilar implantable lead 93 is made, a rubber boot 168, preferably comprised of silicone, is pulled over the crimp connector 100. The rubber boot 168 is a rubber sleeve that is typically pulled over the medical wire 110 before the splice is completed. The rubber boot 168 is slid over the completed splice. Rubber 170, preferably uncured silicone, is injected into the silicone rubber boot 168 to backfill the silicone rubber boot 168 and further seal the crimp connector 100. Sutures 172 can be used to secure the rubber boot 168.

Figure 40:
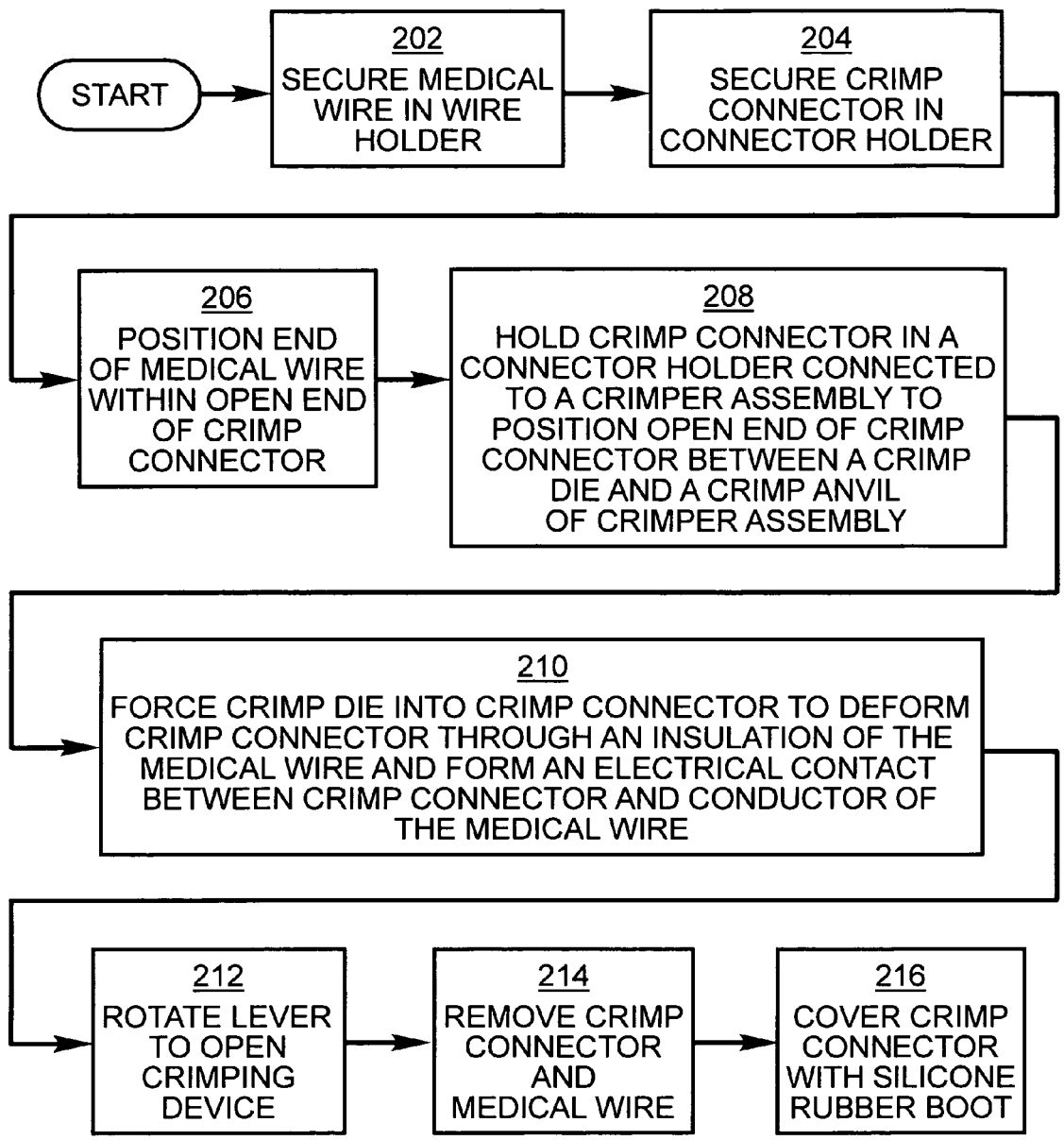
FIG. 40 is a flow chart of a method of connecting a medical wire in accordance with the exemplary embodiment of the invention.

FIG. 40 is a flow chart of a method of connecting a medical wire 110 in accordance with the exemplary embodiment of the invention. Although the method may be performed in a variety of environments and conditions, the method is performed at the surgical implantation site in the exemplary embodiment.

At step 202, the medical wire 110 is secured in the wire holder 30. As described above, the medical wire 110 is slid down the ramp 49 until it moves past the nose 68 of the wire retainer 60 and snaps into the wire groove 38.

At step 204, the crimp connector 100 is secured in the connector holder 40. The crimp connector 100 is slid down the ramp 50 until it moves past the nose 68 of the connector retainer 70 to snap into the groove 48.

At step 206, the end of the medical wire is positioned within the open end of the crimp connector 100. In the exemplary method, the relative positions of the wire holder 30 and the connector holder 40 are changed to move the crimp connector 100 toward the medical wire 110 and placed the open end of the medical wire 110 within the open end of the crimp connector 100.

At step 208, the crimp connector 100 is held in the connector holder to position the open end of the crimp connector 100 between the crimping die 74 and the anvil 20 of the crimper assembly 6. In the exemplary method, the wire holder 30 and the connector holder 40 slide along the pin 54 toward each other to align the open end of the crimp connector 100 between the crimping die 74 and the anvil 20.

At step 210, the crimping die 74 is forced into the crimp connector 100 to deform the crimp connector 100 through the insulation of the medical wire 110 and form an electrical contact between the crimp connector 100 and the conductor of the medical wire 110. The crimping die 74 facilitates crush-penetration of the insulation as it is moved toward the anvil 20.

At step 212, the crimping device 10 is opened. In the exemplary method, the crimp lever 72 is rotated about the pin 54 to open the crimping device 10.

At step 214, the crimp connector 100 and the medical wire 110 are removed. The completed crimp is removed by pulling the crimp connector 100 and the medical wire 110 past the connector retainer 70 and the wire retainer 60, respectively.

At step 216, the crimp connector 100 is covered with a silicone rubber boot. In the exemplary method, the surgeon backfills the boot with uncured silicone and completes the connection by applying sutures to secure the boot. In some circumstances, backfilling, sutures or the boot can be omitted.

Other embodiments and modifications of this invention will occur to those of ordinary skill in the art in view of these teachings. The above description is illustrative and not restrictive. This invention is to be limited only by the following claims, which include all such embodiments and modifications when viewed in conjunction with the above specification and accompanying drawings. The scope of the invention should, therefore, be determined not with reference to the above description, but instead should be determined with reference to the appended claims along with their full scope of equivalents.

What is claimed is:

1. A method of connecting a crimp connector to a wire, the method comprising:
   holding a crimp connector in a connector holder attached to a crimping assembly to position an open end of the crimp connector between a crimp anvil and a crimp die of the crimping assembly;
   holding a wire in a wire holder attached to the crimping assembly to position a portion of the wire within the open end of the crimp connector;
   crimping the crimp connector to the wire; and
   changing the relative position between the connector holder and the wire holder to position the wire within the open end of the crimp connector.

2. The method in accordance with claim 1, wherein changing the relative position comprises moving the connector holder toward the wire holder.

3. The method in accordance with claim 2, wherein changing the relative position comprises moving the wire holder toward the connector holder.

4. The method in accordance with claim 1, wherein changing the relative position comprises moving the wire holder toward the connector holder.

5. The method in accordance with claim 4, wherein changing the relative position further comprises moving the connector holder toward the wire holder.

6. A method of connecting a crimp connector to a wire, the method comprising:
   holding a crimp connector in a connector holder attached to a crimping assembly to position an open end of the crimp connector between a crimp anvil and a crimp die of the crimping assembly;
   holding a wire in a wire holder attached to the crimping assembly to position a portion of the wire within the open end of the crimp connector;
   crimping the crimp connector to the wire; and
   securing the crimp connector in the connector holder with a flexible connector retainer positioned opposite a connector groove of the connector holder, wherein securing the crimp connector comprises sliding the crimp connector down a ramp of the connector holder until audible feedback is received indicating the crimp connector has passed the flexible connector retainer to snap into the connector groove.

7. A method of connecting a crimp connector to a wire, the method comprising:
   holding a crimp connector in a connector holder attached to a crimping assembly to position an open end of the crimp connector between a crimp anvil and a crimp die of the crimping assembly;
   holding a wire in a wire holder attached to the crimping assembly to position a portion of the wire within the open end of the crimp connector;
   crimping the crimp connector to the wire; and
   securing the crimp connector in the connector holder with a flexible connector retainer positioned opposite a connector groove of the connector holder, wherein securing the crimp connector further comprises sliding the crimp connector down a ramp of the connector until tactile feedback is received indicating the crimp connector has passed the flexible connector retainer to snap into the connector groove.

8. A method of connecting a crimp connector to a wire, the method comprising:
   holding a crimp connector in a connector holder attached to a crimping assembly to position an open end of the crimp connector between a crimp anvil and a crimp die of the crimping assembly;
   holding a wire in a wire holder attached to the crimping assembly to position a portion of the wire within the open end of the crimp connector;
   crimping the crimp connector to the wire; and
   securing the wire in the wire holder with a flexible wire retainer positioned opposite a wire groove of the wire holder; wherein securing the wire comprises sliding the wire down a ramp of the wire holder until audible feedback is received indicating the wire has passed the flexible wire retainer to snap into the wire groove.

9. The method in accordance with claim 8 wherein securing the wire further comprises sliding the wire down the ramp until tactile feedback is received indicating the wire has passed the flexible wire retainer to snap into the connector groove.

* * * * *